US011566261B2

United States Patent
Kim et al.

(10) Patent No.: US 11,566,261 B2
(45) Date of Patent: Jan. 31, 2023

(54) **GMPAP2.1 GENE FROM *GLYCINE MAX* CONTROLLING PLANT DISEASE RESISTANCE AGAINST SOYBEAN MOSAIC VIRUS AND USES THEREOF**

(71) Applicant: SEOUL NATIONAL UNIVERSITY R & DB FOUNDATION, Seoul (KR)

(72) Inventors: Kook-Hyung Kim, Seoul (KR); Kristin Widyasari, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 10 days.

(21) Appl. No.: 17/218,398

(22) Filed: Mar. 31, 2021

(65) Prior Publication Data

US 2021/0222191 A1    Jul. 22, 2021

Related U.S. Application Data

(63) Continuation-in-part of application No. PCT/KR2018/013313, filed on Nov. 5, 2018.

(30) Foreign Application Priority Data

Oct. 24, 2018    (KR) .......................... 10-2018-0127200

(51) Int. Cl.
   *C12N 15/82*     (2006.01)
   *A01H 6/54*      (2018.01)
   *C12N 9/16*      (2006.01)

(52) U.S. Cl.
   CPC ......... *C12N 15/8283* (2013.01); *A01H 6/542* (2018.05); *C12N 9/16* (2013.01); *C12Y 301/03002* (2013.01)

(58) Field of Classification Search
   None
   See application file for complete search history.

(56) References Cited

U.S. PATENT DOCUMENTS

| 4,940,838 A | 7/1990 | Schilperoort et al. |
| 2010/0159065 A1 | 6/2010 | Lim |

FOREIGN PATENT DOCUMENTS

| EP | 0 116 718 B1 | 5/1990 |
| EP | 0 120 516 B1 | 10/1991 |
| KR | 10-2004-0084186 A | 10/2004 |
| KR | 10-0857043 B1 | 9/2008 |
| KR | 10-1552140 B1 | 9/2015 |

OTHER PUBLICATIONS

Seo et al 2014 (Scientific Reports 4: p. 1-8) (Year: 2014).*
Kim et al 2012 (PLOS One 7:10, p. 1-12) (Year: 2012).*
Widyasari et al 2022 (Journal of Experimental Botany 73:5, p. 1623-1642) (Year: 2022).*
International Search Report for PCT/KR2018/013313 dated Jul. 22, 2019.
Douglas Hanahan, "Studies on Transformation of *Escherichia coli* with Plasmids", J. Mol. Biol. vol. 166, pp. 557-580, 1983.
Kenneth J. Livak et al., "Analysis of Relative Gene Expression Data Using Real-Time Quantitative PCR and the 2-ΔΔCt Method", Methods, vol. 25, pp. 402-408, 2001.
Jang-Kyun Seo et al., "Type 2C Protein Phosphatase Is a Key Regulator of Antiviral Extreme Resistance Limiting Virus Spread", Scientific Reports vol. 4, 5905, pp. 1-8, 2014.
GenBank:XM_003527817.3 "Predicted: Glycine max purple acid phosphatase 2-like (LOC100789918)", mRNA, 2015.
Jang-Kyun Seo et al., "Protein phosphatase 2C induced by abscisic acid positively regulates Rsv3-mediated extreme resistance", 2015 Joint Symposium of the Korean Society of Breeding Science Next Generation BG21 Business GPS Business. Fusion Tech in Plant Breeding and Globalization of Seed Ind.
Alec J. Hayes et al., "Molecular Marker Mapping of RSV4, a Gene Conferring Resistance to all Known Strains of Soybean Mosaic Virus", Crop Science, vol. 40, pp. 1434-1437, 2000.
Jian-Zhong Liu et al., "The Current Status of the Soybean-Soybean Mosaic Virus (SMV) Pathosystem", Frontiers in Microbiology, vol. 7, 2016.

* cited by examiner

*Primary Examiner* — Matthew R Keogh
(74) *Attorney, Agent, or Firm* — The PL Law Group, PLLC

(57) ABSTRACT

A method according to an embodiment of the present disclosure is for enhancing disease resistance of a plant against Soybean mosaic virus compared to a non-transformant. The method may include transforming a plant cell of the plant with a recombinant vector containing a gene encoding *Glycine max* purple acid phosphatase 2.1 (Gm-PAP2.1) protein from *Glycine max* to overexpress the gene encoding GmPAP2.1 protein. As the GmPAP2.1 gene from *Glycine max* of the present invention can modulate disease resistance against Soybean mosaic virus, it is expected to be applied for development of new cultivars with enhanced resistance to Soybean mosaic virus to thereby increase soybean productivity.

6 Claims, 9 Drawing Sheets

Specification includes a Sequence Listing.

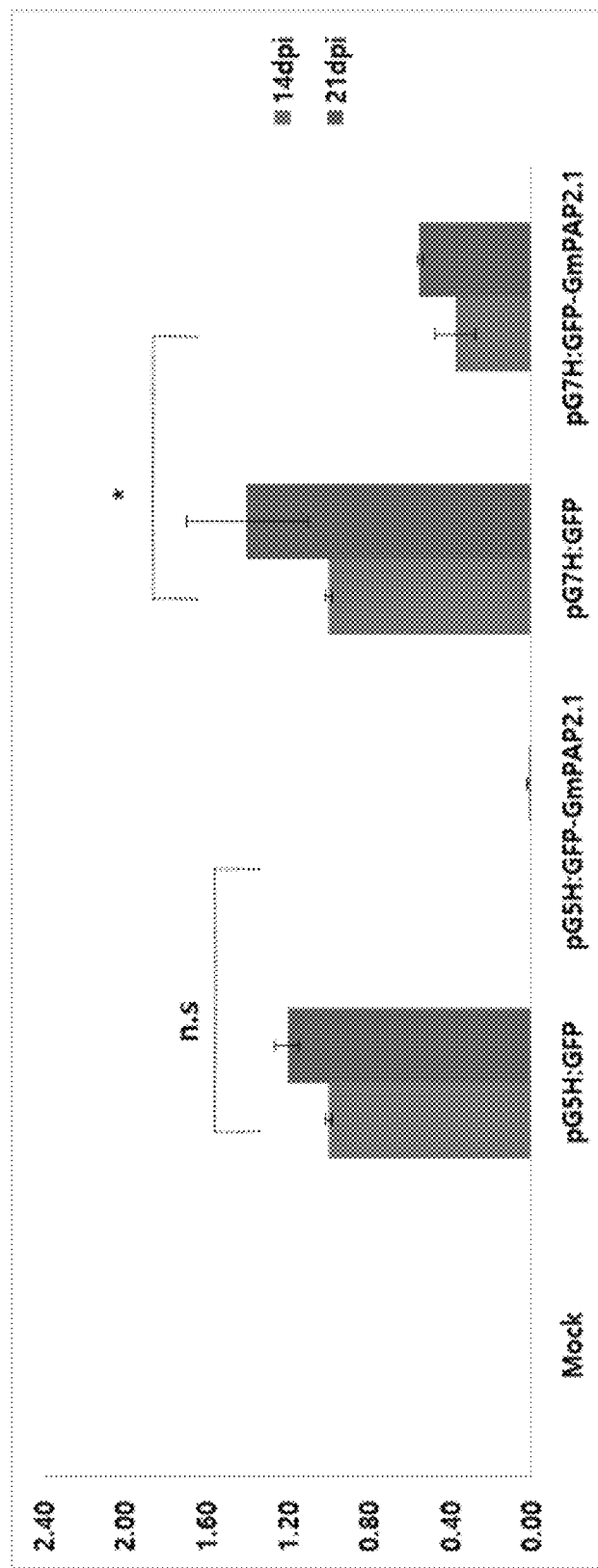

SEQUENCE LISTING

```
<160> NUMBER OF SEQ ID NOS: 13

<210> SEQ ID NO 1
<211> LENGTH: 1230
<212> TYPE: DNA
<213> ORGANISM: Glycine max

<400> SEQUENCE: 1
atggatgaaa agaccactac ttttgtcaga gatgattctt tgtcggtaga tatgccaata      60
gacagtgacg tattccgtgt gcctcctggt tacaacgctc cccaacaggt gcatataaca     120
cagggcgatc acgtggggaa gggtgtgatc atctcttgga ttaccccaca tgaacccggt     180
tcaagcactg tcaaatactg ggccgagaac agtgaattcg aattgaaagc tcatggtttt     240
taccttgctt acaaatactt caattacacc tctggttaca ttcatcactg cactattcac     300
aatttggagt ttgacaccaa atattactat gaggttggaa tagggaatac cactcgacaa     360
ttctggttca aaactcctcc tcctgttggc cccaatgttc cctatacatt tggtctaatt     420
gatgattttc catatcatga caacaccaag tgggatacct ggggaagatt tactgagaga     480
attgcagctt atcagccttg gatttggact gcaggaaatc atgaaattga ttttgctcca     540
gaacttggtg aaaccagacc attcaagcct tacacttgtc gttatcattt accgtacaca     600
gcatcaaata gcacatctcc gttgtggtac tctataaaga gagcttcaac atacatcatt     660
gttttatctt cttactcagc ttttggtaaa tacacgcctc aatacaaatg gcttgtaaag     720
gaactgccca aggtgaacag gacagagacg ccatggctga tagtcctaat gcatagtcca     780
atgtataata gttatgtgaa tcactatatg gaagggagga ccgttagagt attgtacgag     840
aaatggtttg tggaatataa agtcgatgtt gtatttgctg gtcacgttca cgcttatgaa     900
cgatctaaac gggcatcaaa tattgcatat agtattgtaa atgggttgca caaccccatc     960
```

-continued

```
aatgaccaat ctgctccagt ttacataacg attggagatg gaggaaatat agaaggactg    1020
gctactgcta tgacagagcc ccagccaagc tattcagcat accgtgaagc cagttttggg    1080
catggcattc ttgatataaa gaacagaact catgccatt ttagttggaa tcggaatcaa    1140
gatgggtatg cagtggtggc tgattccatt tggttgtaca atagatattg gacccaccca    1200
gaacaaacat ctcttgcatt atttcggtag                                     1230
```

<210> SEQ ID NO 2
<211> LENGTH: 409
<212> TYPE: PRT
<213> ORGANISM: Glycine max

<400> SEQUENCE: 2

```
Met Asp Glu Lys Thr Thr Thr Phe Val Arg Asp Asp Ser Leu Ser Val
1               5                   10                  15

Asp Met Pro Ile Asp Ser Asp Val Phe Arg Val Pro Pro Gly Tyr Asn
            20                  25                  30

Ala Pro Gln Gln Val His Ile Thr Gln Gly Asp His Val Gly Lys Gly
        35                  40                  45

Val Ile Ile Ser Trp Ile Thr Pro His Glu Pro Gly Ser Ser Thr Val
    50                  55                  60

Lys Tyr Trp Ala Glu Asn Ser Glu Phe Glu Leu Lys Ala His Gly Phe
65                  70                  75                  80

Tyr Leu Ala Tyr Lys Tyr Phe Asn Tyr Thr Ser Gly Tyr Ile His His
                85                  90                  95

Cys Thr Ile His Asn Leu Glu Phe Asp Thr Lys Tyr Tyr Tyr Glu Val
            100                 105                 110

Gly Ile Gly Asn Thr Thr Arg Gln Phe Trp Phe Lys Thr Pro Pro
        115                 120                 125

Val Gly Pro Asn Val Pro Tyr Thr Phe Gly Leu Ile Asp Asp Phe Pro
    130                 135                 140

Tyr His Asp Asn Thr Lys Trp Asp Thr Trp Gly Arg Phe Thr Glu Arg
145                 150                 155                 160

Ile Ala Ala Tyr Gln Pro Trp Ile Trp Thr Ala Gly Asn His Glu Ile
                165                 170                 175

Asp Phe Ala Pro Glu Leu Gly Glu Thr Arg Pro Phe Lys Pro Tyr Thr
            180                 185                 190

Cys Arg Tyr His Leu Pro Tyr Thr Ala Ser Asn Ser Thr Ser Pro Leu
        195                 200                 205

Trp Tyr Ser Ile Lys Arg Ala Ser Thr Tyr Ile Ile Val Leu Ser Ser
    210                 215                 220

Tyr Ser Ala Phe Gly Lys Tyr Thr Pro Gln Tyr Lys Trp Leu Val Lys
225                 230                 235                 240

Glu Leu Pro Lys Val Asn Arg Thr Glu Thr Pro Trp Leu Ile Val Leu
                245                 250                 255

Met His Ser Pro Met Tyr Asn Ser Tyr Val Asn His Tyr Met Glu Gly
            260                 265                 270

Glu Thr Val Arg Val Leu Tyr Glu Lys Trp Phe Val Glu Tyr Lys Val
        275                 280                 285

Asp Val Val Phe Ala Gly His Val His Ala Tyr Glu Arg Ser Lys Arg
    290                 295                 300

Ala Ser Asn Ile Ala Tyr Ser Ile Val Asn Gly Leu His Asn Pro Ile
305                 310                 315                 320
```

Asn Asp Gln Ser Ala Pro Val Tyr Ile Thr Ile Gly Asp Gly Asn
            325                 330                 335

Ile Glu Gly Leu Ala Thr Ala Met Thr Glu Pro Gln Pro Ser Tyr Ser
            340                 345                 350

Ala Tyr Arg Glu Ala Ser Phe Gly His Gly Ile Leu Asp Ile Lys Asn
        355                 360                 365

Arg Thr His Ala Tyr Phe Ser Trp Asn Arg Asn Gln Asp Gly Tyr Ala
    370                 375                 380

Val Val Ala Asp Ser Ile Trp Leu Tyr Asn Arg Tyr Trp Thr His Pro
385                 390                 395                 400

Glu Gln Thr Ser Leu Ala Leu Phe Arg
            405

<210> SEQ ID NO 3
<211> LENGTH: 153
<212> TYPE: PRT
<213> ORGANISM: Glycine max

<400> SEQUENCE: 3

Met His Ser Pro Met Tyr Asn Ser Tyr Val Asn His Tyr Met Glu Gly
1               5                   10                  15

Glu Thr Val Arg Val Leu Tyr Glu Lys Trp Phe Val Glu Tyr Lys Val
            20                  25                  30

Asp Val Val Phe Ala Gly His Val His Ala Tyr Glu Arg Ser Lys Arg
        35                  40                  45

Ala Ser Asn Ile Ala Tyr Ser Ile Val Asn Gly Leu His Asn Pro Ile
    50                  55                  60

Asn Asp Gln Ser Ala Pro Val Tyr Ile Thr Ile Gly Asp Gly Gly Asn
65                  70                  75                  80

Ile Glu Gly Leu Ala Thr Ala Met Thr Glu Pro Gln Pro Ser Tyr Ser
                85                  90                  95

Ala Tyr Arg Glu Ala Ser Phe Gly His Gly Ile Leu Asp Ile Lys Asn
            100                 105                 110

Arg Thr His Ala Tyr Phe Ser Trp Asn Arg Asn Gln Asp Gly Tyr Ala
        115                 120                 125

Val Val Ala Asp Ser Ile Trp Leu Tyr Asn Arg Tyr Trp Thr His Pro
    130                 135                 140

Glu Gln Thr Ser Leu Ala Leu Phe Arg
145                 150

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
gctctagagt gagcaagggc gaggagctg                                    29

<210> SEQ ID NO 5
<211> LENGTH: 50
<212> TYPE: DNA
<213> ORGANISM: Artificial Sequence
<220> FEATURE:
<223> OTHER INFORMATION: primer -continued

<400> SEQUENCE: 5
gcacgcgtga ctgtaaagat acggactcct tgtacagctc gtccatgccg          50

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
gcacgcgtat ggatgaaaag accacta                                    27

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gcacgcgtcc gaaataatgc aagaga                                     26

<210> SEQ ID NO 8
<211> LENGTH: 39
<212> TYPE: DNA
<213> ORGANISM: Artificial Sequence
<220> FEATURE:
<223> OTHER INFORMATION: primer

<400> SEQUENCE: 8
gcacgcgtat gcatagtcca atgtataata gttatgtga                       39

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
gcacgcgtta ggactatcag ccatgg                                     26

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aaggctgcag ctctctcggg                                            20

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
tcacatccct tgcagtatgc ctt                                        23

<210> SEQ ID NO 12

```
<211> LENGTH: 25
<212> TYPE: DNA
<213> ORGANISM: Artificial Sequence
<220> FEATURE:
<223> OTHER INFORMATION: primer

<400> SEQUENCE: 12
agtaaagagc accatgccta tccac                                              25

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
atggttatgt gagcagatgc aaggc                                              25
```

GMPAP2.1 GENE FROM *GLYCINE MAX* CONTROLLING PLANT DISEASE RESISTANCE AGAINST SOYBEAN MOSAIC VIRUS AND USES THEREOF

CROSS REFERENCE TO RELATED APPLICATIONS

The present application is a continuation in part application to International Application No. PCT/KR2018/013313 with an International Filing Date of Nov. 5, 2018, which claims the benefit of Korean Patent Application No. 10-2018-0127200, filed in the Korean Intellectual Property Office on Oct. 24, 2018, the entire contents of which are incorporated herein by reference.

BACKGROUND

1. Technical Field

The present invention relates to GmPAP2.1 gene from *Glycine max* controlling plant disease resistance against Soybean mosaic virus and uses thereof.

2. Background Art

Soybean (*Glycine max*) is an annual dicot plant belonging to the family Leguminosae of the order Rosales and it is known to originate from Northeast Asia including Korean peninsula. About 13,000 species of 550 genera are known all over the world, and, in South Korea, 92 species of 36 genera are naturally found. Soybean has been utilized as a source of protein and fat, and it is also a crop currently attracting attention as an industrial material.

Soybean mosaic virus (SMV) is a virus belonging to Potyvirus of the family Potyviridae. Insect transmission of the virus is caused by aphids, and it is reported that up to 43% seed transmission occurs in soybean. The virus causes a decrease in the number of pods, a decrease in the number of seeds per pod, a decrease in the size and weight of a seed, generation of stains on soybean husk, or the like that are directly related to the productivity of soybean.

In plants, gene-mediated resistance is one of the defense mechanisms for preventing or reducing virus infection, and plant resistance genes are classified into dominant genes and recessive genes. While the recessive resistance genes provide passive resistance in which virus propagation is not appropriately exhibited due to the incompatible interaction between the virus and host elements, the dominant resistance genes (R gene) encode the resistance protein (R protein) which recognizes pathogen effector or avirulence (Avr) element, thus providing active resistance. In general, R gene encodes the proteins having nucleotide-binding site (NBS) and leucine-rich repeat (LRR) site. NBS domain can bind to ATP (Adenosine Tri-Phosphate) for hydrolysis, and it is composed of a functional nucleotide-binding pocket showing signaling resistance response. LPR domain is composed of separate repeats of common leucine-rich repeat motif and is found to be related with Avr recognition. NBS-LRR proteins are divided into two groups; i.e., TIR-NBS-LRR protein including N-terminal domain which has Toll/interleukin-1 receptor homology and CC-NBS-LRR protein characterized by N-terminal coiled-coil motif.

In South Korea, total 11 lines are reported as Soybean mosaic virus (i.e., G1 to G7, G5H, G6H, G7H, and G7a), and new lines overcoming the resistance gene are continuously found. As a resistance gene showing resistance to Soybean mosaic virus which is known at present moment, there are Rsv1 (R genes against SMV), Rsv3 and Rsv4. Rsv1 is identified from chromosome 13 of PI 96983, which is native soybean species in South Korea. Three NBS-LRR sequences, i.e., 3gG2, 5gG3 and 6gG9, are present near the Rsv1 gene locus, and at least one of them is responsible for the Rsv1 resistance. Rsv3 is mapped between A519F/R and M3Satt, which are molecular markers of chromosome 14 of soybean cultivar L29. In the 154 kbp region between the two markers, 5 candidate genes including NBS-LRR domain are present (i.e., Glyma.14g204500, Glyma.14g204600, Glyma.14g204700, Glyma.14g205000 and Glyma.14g205300), and Glyma.14g204700 is particularly known to be related with the Rsv3 resistance. In addition, Rsv4 is mapped between Rat2 and S6a, which are molecular markers of chromosome 2 of soybean cultivar VP-5152. R gene of NBS-LRR type is not identified from Rsv4, indicating that Rsv4 belongs to resistance genes of novel class.

In Korean Patent Registration No. 1552140, "Transgenic soybean plant with enhanced resistance to Soybean mosaic virus based on gene silencing of HC-Pro gene and method of producing the same" is disclosed, and in Korean Patent Registration No. 0857043, "Specific primer for diagnosis of Soybean mosaic virus" is disclosed. However, GmPAP2.1 gene from *Glycine max* controlling plant disease resistance against Soybean mosaic virus of the present invention and uses thereof have not been described.

SUMMARY

Inventors of the present invention found that expression of GmPAP2.1 (*Glycine max* purple acid phosphatase 2.1) gene present at chromosome 6 of *Glycine max* cultivar L29 is enhanced according to the infection with Soybean mosaic virus (SMV), and, as a result of analyzing the disease resistance against SMV after transforming a plant with a recombinant vector encoding the full-length GmPAP2.1 protein or a variant of GmPAP2.1 protein with N-terminal deletion or C-terminal deletion, the inventors found that the transgenic plant expressing full-length GmPAP2.1 protein or N-terminal deletion variant exhibits high resistance against SMV while the transgenic plant expressing C-terminal deletion variant of GmPAP2.1 exhibits lower resistance against SMV. Accordingly, it is recognized that GmPAP2.1 protein provides a soybean plant with resistance against SMV, and, in particular, the C-terminal is a key domain related to the disease resistance against SMV. The present invention is completed accordingly.

To solve one or more of the problems that are described in the above, an embodiment of the present invention provides a method of enhancing disease resistance of a plant against Soybean mosaic virus compared to a non-transformant, said method including transforming a plant cell with a recombinant vector containing a gene encoding GmPAP2.1 (*Glycine max* purple acid phosphatase 2.1) protein from *Glycine max* to overexpress the gene encoding GmPAP2.1 protein.

An embodiment of the present invention provides a method of producing a transgenic plant having enhanced disease resistance against Soybean mosaic virus compared to a non-transformant, said method including: transforming a plant cell with a recombinant vector containing a gene encoding GmPAP2.1 protein from *Glycine max*; and regenerating a plant from the transformed plant cell.

An embodiment of the present invention provides a transgenic plant having enhanced disease resistance against Soybean mosaic virus produced by the aforementioned method, and a transgenic seed thereof.

An embodiment of the present invention provides a composition for enhancing disease resistance of a plant against Soybean mosaic virus including, as an effective component, a gene encoding GmPAP2.1 protein from *Glycine max* which consists of the amino acid sequence of SEQ ID NO: 2 or SEQ ID NO: 3.

As the disease resistance against Soybean mosaic virus can be modulated by GmPAP2.1 gene derived from *Glycine max* of the present invention, it is expected that new cultivars with enhanced resistance to Soybean mosaic virus can be developed to thereby increase soybean productivity.

BRIEF DESCRIPTION OF THE DRAWINGS

FIG. 1 is a schematic diagram showing the process of rub-inoculation for control group (Mock; 20× potassium phosphate buffer) and GFP (green fluorescent protein)-tagged plasmid (pG5H:GFP or pG5H:GFP-GmPAP2.1).

Figure 2A:
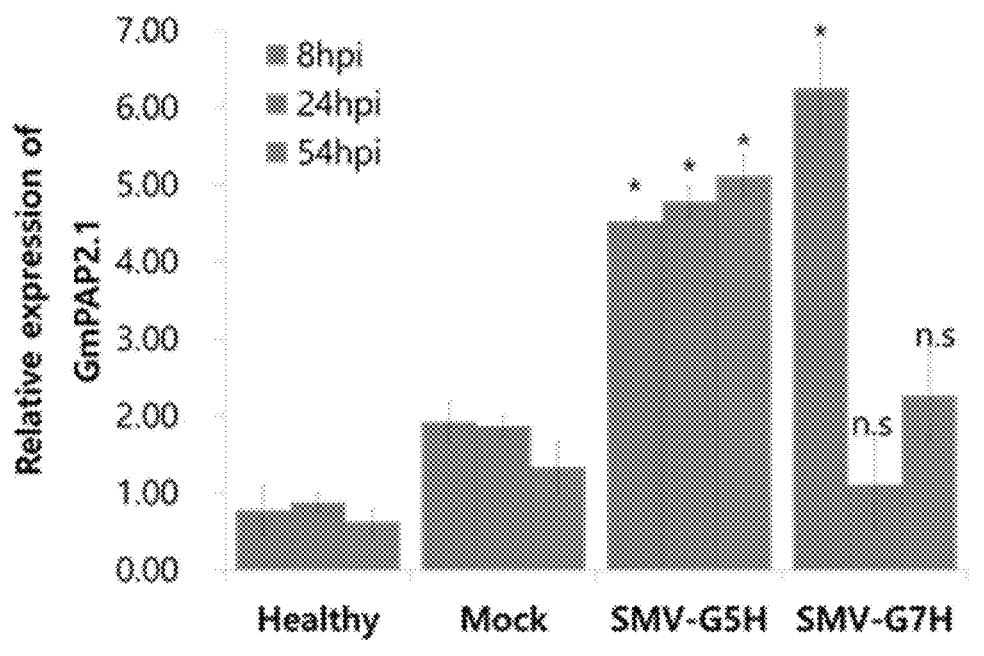

FIG. 2A shows the expression level of Gm06g028100 (GmPAP2.1) gene in *Glycine max*, which has been infected with G5H or G7H as a Soybean mosaic virus.

FIG. 4B shows a graph illustrating the expression level of viral RNA. In the figure, dpi represents day post infection, and for the statistical comparison between pG5H:GFP-GmPAP2.1 or pG7H:GFP-GmPAP2.1 and positive control group pG5H:GFP or pG7H:GFP, unpaired 2-tailed T-test was employed (*:P<0.05, ns (not significant): P>0.05).

DETAILED DESCRIPTION

Figure 2B:
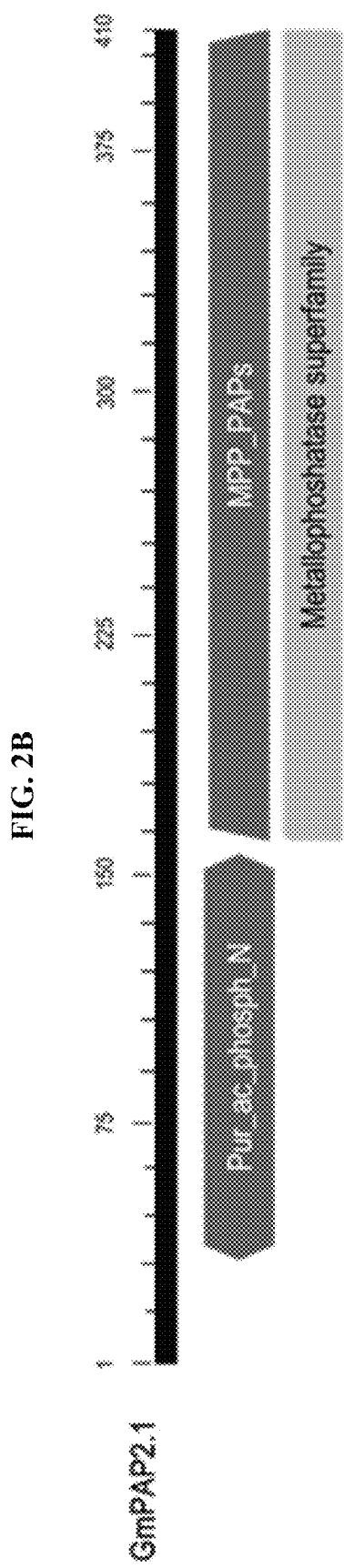
FIG. 2B shows the prediction of a target protein based on nucleotide sequencing of Gm06g028100 gene.

To achieve one or more aspects of the present invention, an embodiment of the present invention provides a method of enhancing disease resistance of a plant against Soybean mosaic virus compared to a non-transformant, said method including transforming a plant cell with a recombinant vector containing a gene encoding GmPAP2.1 (*Glycine max* purple acid phosphatase 2.1) protein from *Glycine max* to overexpress the gene encoding GmPAP2.1 protein.

The GmPAP2.1 protein from *Glycine max* may indicate the C-terminal of GmPAP2.1 protein or GmPAP2.1 protein including the C-terminal, and, for example, it may consist of the amino acid sequence of SEQ ID NO: 2 or SEQ ID NO: 3, but not limited thereto. SEQ ID NO: 2 means the entire amino acid sequence of GmPAP2.1 protein and SEQ ID NO: 3 means the amino acid sequence of C-terminal region of GmPAP2.1 protein. Specifically, SEQ ID NO: 3 represent the amino acid sequence having the $257^{th}$ to $409^{th}$ amino acids in the amino acid sequence of SEQ ID NO: 2.

Also included in the scope of the GmPAP2.1 protein of the present invention are the proteins having an amino acid sequence represented by SEQ ID NO: 2 or SEQ ID NO: 3, and functional equivalents thereof.

As described herein, the term "functional equivalents" means a protein which has, as a result of addition, substitution, or deletion of an amino acid, at least 70%, preferably at least 80%, more preferably at least 90%, and even more preferably at least 95% sequence homology with the amino acid sequence represented by SEQ ID NO: 2 or 3, and it indicates a protein which exhibits substantially the same physiological activity as the protein represented by SEQ ID NO: 2 or 3. The expression "substantially the same physiological activity" indicates an activity of enhancing the resistance against SMV. Also included in the present invention are fragments, derivatives, and analogues of GmPAP2.1 protein.

As described herein, the terms "fragments", "derivatives", and "analogs" indicate a polypeptide having substantially the same function or activity as GmPAP2.1 polypeptide of the present invention. The "fragments", "derivatives", and "analogs" of the present invention can be (i) a polypeptide in which one or more conservative or non-conservative amino acid residues (preferably, conservative amino acid residues) are substituted (substituted amino acid residues may be encoded or not encoded by genetic code), (ii) a polypeptide having substituent(s) at one or more amino acid residues, (iii) a polypeptide derived from mature polypeptide that is linked with other compound (i.e., compound allowing extended half life of the polypeptide, for example, polyethylene glycol), or (iv) a polypeptide derived from the aforementioned polypeptide that is linked with an additional amino acid sequence (for example, leading sequence, secretion sequence, sequence used for purification of the polypeptide, proteinogen sequence, or fusion protein). The fragments, derivatives, and analogs defined in the present invention are well known to a person who is skilled in the pertinent art.

Further, the gene encoding the aforementioned GmPAP2.1 protein is characterized in that it can modulate the disease resistance against SMV, and the gene has the scope to encompass all genomic DNA, cDNA, and synthetic DNA encoding GmPAP2.1 protein. For example, the gene encoding GmPAP2.1 protein of the present invention may consist of the nucleotide sequence of SEQ ID NO: 1. Furthermore, homologs of the aforementioned sequence is within the scope of the present invention. Specifically, the aforementioned gene may include a nucleotide sequence which has 70% or higher, more preferably 80% or higher, even more preferably 90% or higher, and most preferably 95% or higher sequence homology with the nucleotide sequence of SEQ ID NO: 1. The "sequence homology %" of the polynucleotide is identified by comparing two sequences that are optimally aligned. In this regard, a part of the polynucleotide in comparative region may include an addition or a deletion (i.e., a gap) compared to a reference sequence (without any addition or deletion) in the optimized alignment of the two sequences.

As described herein, the term "recombinant" indicates a cell which replicates an exogenous nucleotide or expresses the nucleotide, or a cell which expresses a peptide, an exogenous peptide, or a protein encoded by an exogenous nucleotide. Recombinant cell can express a gene or a gene fragment, which is not found in natural-state cell, in the form of a sense or an antisense. In addition, the recombinant cell can express a gene that is found in natural state, provided that said gene is modified and re-introduced into the cell by an artificial means.

As described herein, the "vector" is used for indicating a means for delivering DNA fragment(s) or genetic molecules to cells. Vector allows replication of DNA and it can be independently re-produced in host cells. The term "delivery vehicle" is used interchangeably with "vector".

The vector of the present invention can be constructed typically as a vector for expression or cloning. Furthermore, the vector of the present invention can be constructed by using a prokaryotic cell or an eukaryotic cell as a host. For example, when the vector of the present invention is an expression vector and a prokaryotic cell is used as a host, it generally includes a potent promoter capable of conducting transcription (such as pLλ promoted, trp promoter, lac promoter, T7 promoter, tac promoter, or the like), a ribosome-binding site for initiation of translation, and a transcription/translation termination sequence. In addition, when $Escherichia\ coli$ is used as a host cell, the promoter and operator sites for the pathway of tryptophan biosynthesis in $E.\ coli$ and the left promoter of phage λ (pLλ promoter) can be utilized as a regulation site.

With regard to the recombinant vector of the present invention, the promoter is a promoter which is suitable for transformation. For example, it may be any one of CaMV 35S promoter, actin promoter, ubiquitin promoter, pEMU promoter, MAS promoter or histone promoter. For example, it may be CaMV 35S promoter, but not limited thereto.

As described herein, the term "promoter" means a DNA region located upstream of a structure gene, and it indicates a DNA molecule to which RNA polymerase binds to initiate the transcription. The term "plant promoter" means a promoter allowing transcription in plant cell. The term "constitutive promoter" indicates a promoter which is active in most of environmental conditions and development states or cell differentiation states. Since a transformant can be selected with various mechanisms at various stages, a constitutive promoter may be preferable. Therefore, a possibility for choosing a constitutive promoter is not limited herein.

The recombinant vector of the present invention can be constructed by a method which is well known to a person skilled in the art. Examples of such method include an in vitro recombination DNA technique, a DNA synthesis technique, and an in vivo recombination technique. The DNA sequence may be effectively linked to a suitable promoter in the expression vector in order to induce synthesis of mRNA. Furthermore, the expression vector may contain, as a site for translation initiation, a ribosome binding site and a transcription terminator.

An example of the recombinant vector of the present invention is Ti-plasmid vector which can transfer a part of itself, i.e., so called T-region, to a plant cell when the vector is present in an appropriate host such as $Agrobacterium\ tumefaciens$. Other types of Ti-plasmid vector (see, EP 0 116 718 B1) are currently used for transferring a hybrid DNA sequence to protoplasts that can produce a new plant by appropriately inserting a plant cell or hybrid DNA to a genome of a plant. Especially preferred form of Ti-plasmid vector is a so-called binary vector which has been claimed in EP 0 120 516 B1 and U.S. Pat. No. 4,940,838. Other vector that can be used for introducing the DNA of the present invention to a host plant can be selected from a double-stranded plant virus (e.g., CaMV), a single-stranded plant virus, and a viral vector which may originate from Gemini virus, etc., for example a non-complete plant viral vector. Use of said vector can be particularly advantageous when a plant host cannot be easily transformed.

The recombinant expression vector may contain one or more selective marker. The selective marker is a nucleotide sequence having a property of allowing vector selection by a common chemical method. Any gene that can be used for identifying transformed cells from non-transformed cells can be a selective marker. Examples of the marker gene include an antibiotics resistance gene, but it is not limited thereto.

A common terminator can be used for the recombinant vector of the present invention, and examples thereof include nopaline synthase (NOS), rice α-amylase RAmy1 A terminator, a phaseolin terminator, a terminator for octopine gene of $Agrobacterium\ tumefaciens$, or the like, but it is not limited thereto. With regard to the necessity of a terminator, it is generally known that such region can enhance the certainty and efficiency of transcription in plant cells. As such, use of a terminator is highly desirable in the context of the present invention.

In case of transforming an eukaryotic cell with the vector of the present invention, yeast ($Saccharomyce\ cerevisiae$), an insect cell, human cell (e.g., CHO (Chinese hamster ovary) cell line, W138, BHK, COS-7, 293, HepG2, 3T3, RIN and MDCK cell line), a plant cell, or the like can be used as a host cell. For example, the host cell is a plant cell.

When the host cell is a prokaryotic cell, the method of delivering the vector of the present invention to a host cell can be carried out by $CaCl_2$ method, Hanahan's method (Hanahan, D., 1983 J. Mol. Biol. 166, 557-580), electroporation, or the like. When the host cell is an eukaryotic cell, the vector can be incorporated to a host cell by microinjection, calcium phosphate precipitation, electroporation, liposome-mediated transfection, DEAE-dextran treatment, gene bombardment, or the like.

An embodiment of the present invention also provides a method of producing a transgenic plant having enhanced disease resistance against Soybean mosaic virus compared to a non-transformant, said method including: transforming a plant cell with a recombinant vector containing a gene encoding GmPAP2.1 protein from $Glycine\ max$; and regenerating a plant from the transformed plant cell.

With regard to the method of an embodiment of the present invention for producing a transgenic plant having enhanced disease resistance against Soybean mosaic virus in plant, scope of the GmPAP2.1 protein is the same as described in the above.

Plant transformation means any means for transferring a DNA to plant. Such transformation method does not necessarily require a period for regeneration and/or tissue culture. Transformation of plant species is now quite common not only for dicot plants but also for monocot plants. In principle, any transformation method can be used for introducing a hybrid DNA of the present invention to appropriate progenitor cells. The method can be appropriately selected from a calcium/polyethylene glycol method for protoplasts, an electroporation method for protoplasts, a microscopic injection method for plant components, a (DNA or RNA-coated) particle bombardment method for various plant components (non-complete) viral infection method in *Agrobacterium tumefaciens* mediated gene transfer by plant invasion or transformation of fully ripened pollen or microspore, etc. An exemplary method according to the present invention includes *Agrobacterium*-mediated DNA delivery.

Further, as for the method for regenerating a transgenic plant from a transformed plant cell, a method well known in the pertinent art can be used. The transformed plant cell needs to be regenerated into a whole plant. Techniques for regeneration into a mature plant by culture of callus or protoplast are well known in the pertinent art for various species.

An embodiment of the present invention provides a transgenic plant having enhanced disease resistance against Soybean mosaic virus produced by the aforementioned method, and a transgenic seed of the transgenic plant.

According to one embodiment of the present invention, the plant used for the present invention can be a plant which belongs to the family Fabacea. For example, the plant can be soybean, mung bean, kidney bean, sweet pea, lentil bean, black eyed pea, red bean, or the like, and it is not limited to them as long as the plant is a host plant of Soybean mosaic virus.

An embodiment of the present invention provides a composition for enhancing disease resistance of a plant against Soybean mosaic virus including, as an effective component, a gene encoding GmPAP2.1 protein from *Glycine max* which consists of the amino acid sequence of SEQ ID NO: 2 or SEQ ID NO: 3.

The composition includes, as an effective component, a gene encoding the amino acid sequence of SEQ ID NO: 2 or SEQ ID NO: 3 or a recombinant vector containing the gene, and the disease resistance of a soybean plant against Soybean mosaic virus can be enhanced according to transformation of soybean plant with the gene.

Hereinbelow, the present invention is explained in detail in view of the examples. However, the following examples are given only for exemplification of the present invention, and it is evident that the present invention is not limited to the following examples.

EXAMPLES

Materials and Methods
1. Plant Material

*Glycine max* cultivar L29 (Rsv3) and Lee 74 were obtained from Culture Environment Department of Central Crop Group of Korean National Institute of Crop Science, and they were grown in a growth chamber at 25° C. under 16 h/8 h photoperiod. Cultivar L29 was used as a subject plant for extraction of total RNA to have cDNA synthesis while Lee 74 was used as a subject plant for transformation. Soybean seedlings for virus vector inoculation were selected when the first primary leaves were fully expanded.

2. Preparation of GFP-Tagged Viral Vector

The coding region of GFP (Green Fluorescent Protein) gene without the start and stop codons (714 bp) was amplified by PCR. Information of the primers used for the PCR is shown in the following Table 1, and PCR was performed for 35 cycles using Ex Taq polymerase (TaKaRa, Japan). The PCR amplified product was digested with restriction enzymes MluI and XbaI, and then ligated to MCS (Multiple Cloning Site) of viral expression vector based on SMV-G5H (pG5H) and SMV-G7H (pG7H). The product finally obtained was named as pG5H::GFP.

TABLE 1

Primer information

| Primer Name | Nucleotide Sequence (5'?+0+223') |
|---|---|
| GFP_F | 5'-GC*TCTAGA*GTGAGCAAGGGCGAGGAGCTG-3' (SEQ ID NO: 4) (italic letters: restriction enzyme *XbaI* site |
| GFP_R | 5'-GC*ACGCGT*<u>GACTGTAAAGATACGGACTCC</u>TTGTACAGCTCGTC CATGCCG-3' (SEQ ID NO: 5) (italic letters: restriction enzyme *MluI* site, underlined letters: coding region in NIa protease recognition site) |

3. Construction of Viral Vector Overexpressing GmPAP2.1 Protein and Mutants

The coding region of GmPAP2.1 without stop codon was amplified from the cDNA of *Glycine max* cultivar L29. To obtain the expression clones, the amplified product was digested with MluI and cloned into pG5H::GFP. The product finally obtained was named as pG5H::GFP-GmPAP2.1. Furthermore, mutant clones (pG5H:GFP-GmPAP2.1_N (C-terminal deletion: Δ257-409aa) and pG5H:GFP-GmPAP2.1_C (N-terminal deletion: Δ1-256aa)) were constructed in the same manner as the above. The coding region of each mutant was amplified from the plasmid DNA of pG5H::GFP-GmPAP2.1. Information of the primers used for the construction of mutant clones are the same as described in the following Table 2. Insertion of the target gene or target gene fragment in the viral vector was determined by colony PCR and sequencing.

TABLE 2

Primer information

| Primer Name | Use | Nucleotide Sequence (5'→3') |
|---|---|---|
| GmPAP2.1_F | GmPAP2.1 cloning | gcacgcgtATGGATGAAAAGACCACTA (SEQ ID NO: 6) |
| GmPAP2.1_R | GmPAP2.1 cloning | gcacgcgt CCGAAATAATGCAAGAGA (SEQ ID No: 7) |
| A1-256aa_F | N-terminal deletion GmPAP2.1 cloning | gcacgcgtATGCATAGTCCAATGTATAATAGTTAT GTGA (SEQ ID NO: 8) |
| A1-256aa_R | N-terminal deletion GmPAP2.1 cloning | gcacgcgtCCGAAATAATGCAAGAGA (SEQ ID NO: 7) |
| 4257-409aa_F | C-terminal deletion GmPAP2.1 cloning | gcacgcgtATGGATGAAAAGACCACTA (SEQ ID NO: 6) |
| 4257-409aa_R | C-terminal deletion GmPAP2.1 cloning | gcacgcgtTAGGACTATCAGCCATGG (SEQ ID NO: 9) |

Bold letters; restriction enzyme site (MluI).

4. Inoculation Using Viral Vector and Visual Assessment

Figure 1:
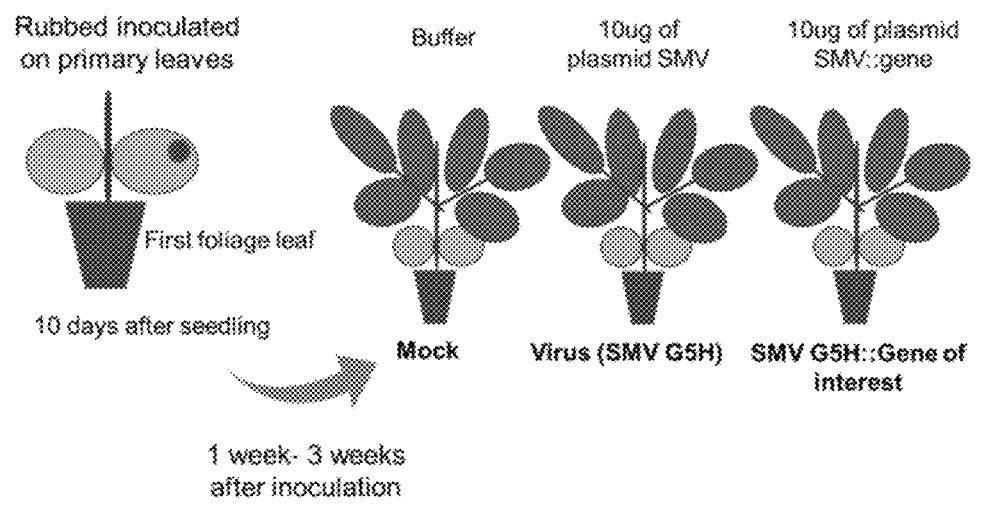

Inoculation of empty vector and virus expression clone were conducted by rub-inoculation of the plasmid DNA onto primary leaves of soybean cultivar Lee 74 (Rsv3-free). Plasmid DNA was prepared using the Plasmid Maxi Kit (QIAGEN, USA). For each leaves, 20 µl mixture solution containing 10 µg of plasmid DNA clone and 20× potassium phosphate buffer (pH 7.5 with final concentration 1×) was rub-inoculated. The experiment was repeated three times by using plants inoculated with Mock group (20× potassium phosphate buffer), vector control (pG5H:GFP), or expression clone (pG5H:GFP-GmPAP2.1, pG5H:GFP-GmPAP2.1_N or pG5H:GFP-GmPAP2.1_C) (FIG. 1). Systemic expression of GFP in the infected plant was visualized under UV illumination with a hand-held UV-light source, and fluorescence signals emitted by GFP in cells of inoculated soybean primary leaves were determined by a fluorescence microscopy (Axiovert, USA).

5. RNA Extraction and qRT-PCR

From the each primary leaf, total RNA was extracted by using RNAiSO plus reagent method (TaKaRa) and cDNA was synthesized using GoScript reverse transcriptase (Promega Corp., USA) and oligo(dT) primer (15mer, Bioneer). Viral RNA replication was carried out by partial amplification of coat protein (CP) region of SMV-G5H. The short fragment of CDPK (Calcium dependent protein kinase) gene from *Glycine max* was used as an internal control for standardization of other samples, and the information of primers for amplifying the coat protein fragment of SMV-G5H and CDPK gene are described in the following Table 3. The above experiment was repeated three times.

TABLE 3

Primer information

| Primer Name | Nucleotide Sequence (5'→3') |
|---|---|
| SMV-G5H-CP_F | 5'-AAGGCTGCAGCTCTCTCGGG-3' (SEQ ID NO: 10) |
| SMV-G5H-CP_R | 5'-TCACATCCCT-TGCAGTATGCCTT-3' (SEQ ID NO: 11) |

TABLE 3-continued

Primer information

| Primer Name | Nucleotide Sequence (5'→3') |
|---|---|
| CDPK_F | 5'-AGTAAAGAGCACCATGCCTATCCAC-3' (SEQ ID NO: 12) |
| CDPK_R | 5'-ATGGTTATGTGAGCAGATGCAAGGC-3'. (SEQ ID NO: 13) |

Relative quantification was performed according to the $2^{-\Delta\Delta Ct}$ method (Kenneth J. L., 2001, METHODS, 25, 402-408, 2001), and the results from qRT-PCR were analyzed by calculating mean and standard deviation by using Microsoft Excel 2010 (Microsoft, USA).

Example 1. Analysis of GmPAP2.1 Gene from *Glycine max* Cultivar L29

As a result of performing qRT-PCR, it was found that expression of Gm06g028100 gene of L29 cultivar has increased by initial infection with G5H and G7H as SMV, and, 8 hours after the infection in particular, the expression of Gm06g028100 gene has increased by approximately 4 times compared to the plant without any infection. Accordingly, it was recognized that Gm06g028100 gene is related with the resistance against SMV (FIG. 2A). Furthermore, as a result of analyzing the nucleotide sequence of Gm06g028100 gene, it was considered that it may encode a purple acid phosphatase-like protein, which is a superfamily metalophosphatase (FIG. 2B).

Figure 2C:
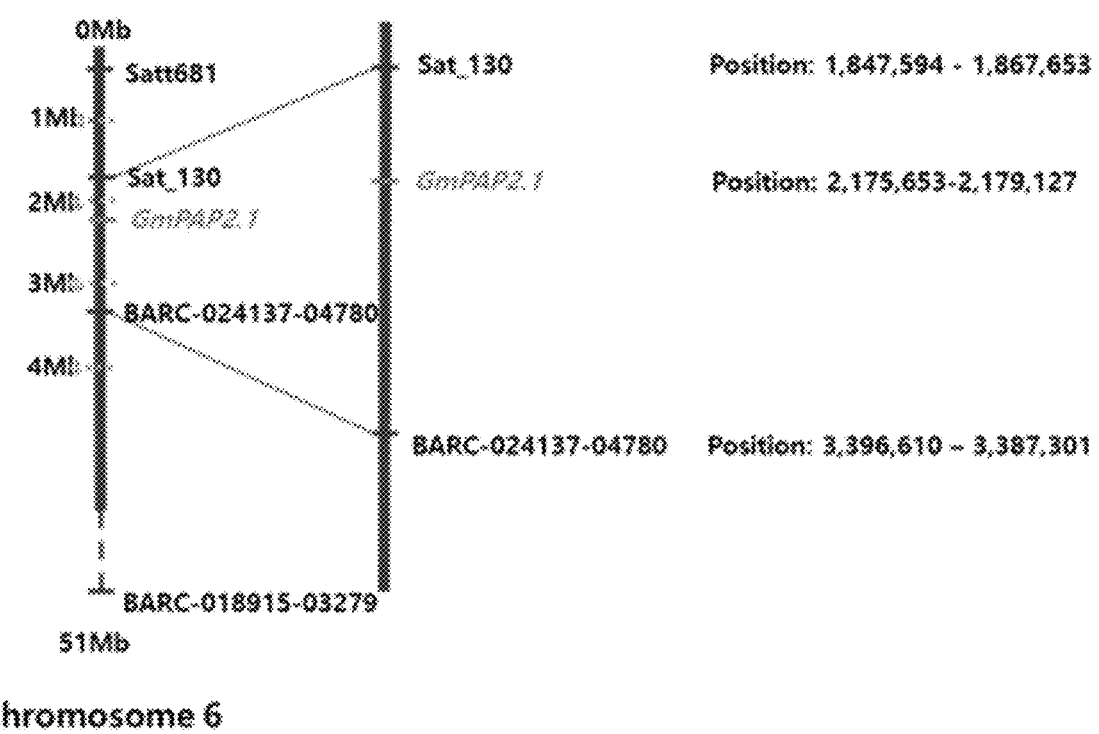
FIG. 2C shows the result of determining the location of Gm06g028100 gene based on chromosome analysis of *Glycine max* cultivar L29. In the figure, hpi represents hour post infection.

In *Glycine max* cultivar L29, Rsv3 gene is known to be present in chromosome 14 showing strong resistance against SMV-G5H. However, Gm06g028100 gene is present between molecular markers Sat130 and BARC_024137_04780 in chromosome 6 and not found near Rsv3 gene. As such, it is recognized that Gm06g028100 gene does not have any relationship with Rsv3 gene (FIG. 2C).

Figure 3:
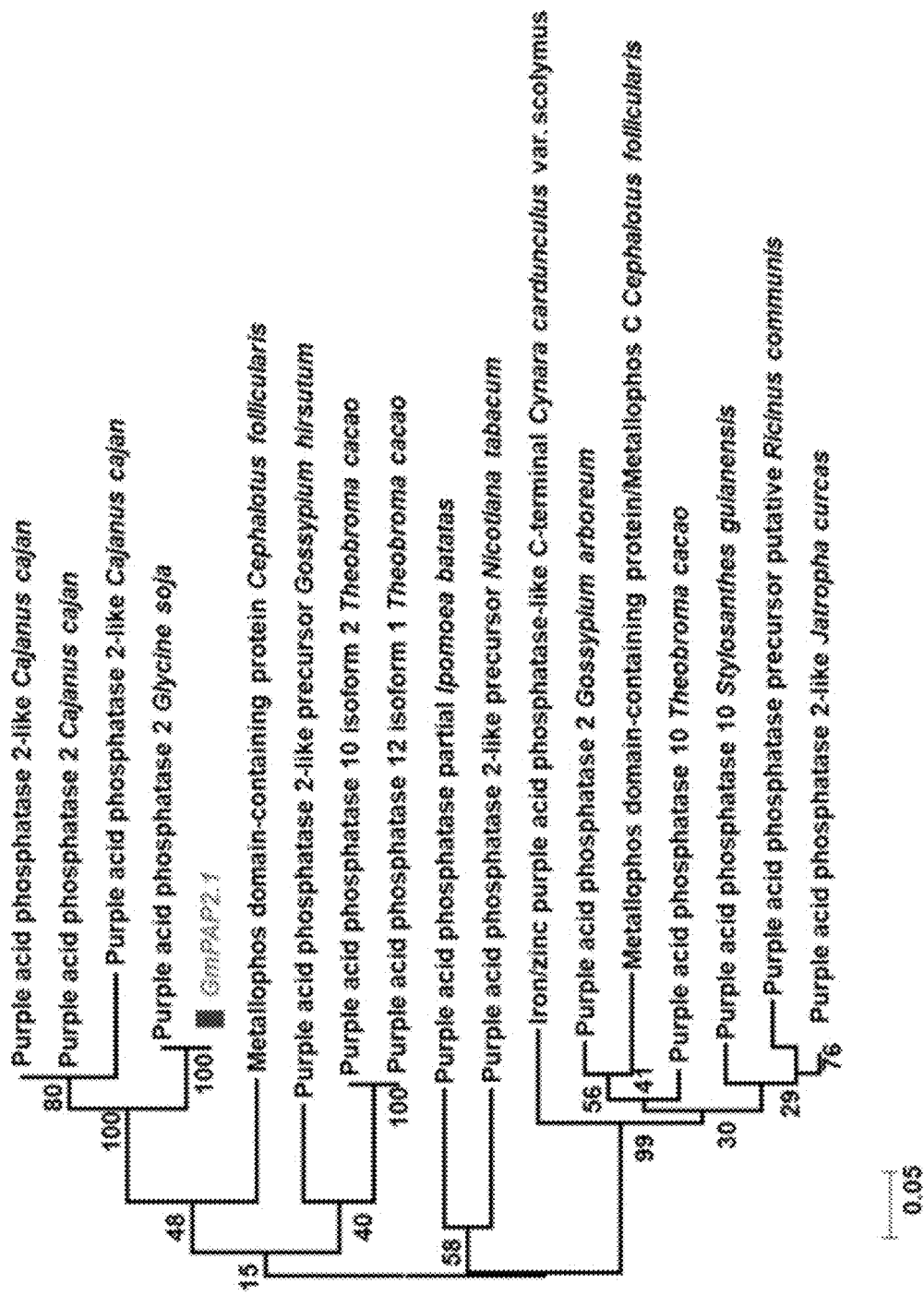
FIG. 3 shows the phylogenetic analysis result of the putative domain of Gm06g028100 gene.

In addition, as a result of performing phylogenetic analysis for the putative domain of Gm06g028100 gene, it was found to be related to purple acid phosphatase 2 of *Glycine soja*, and Gm06g028100 gene was named as GmPAP2.1 (FIG. 3).

Example 2. Analysis of Resistance of GmPAP2.1 Gene Against SMV

In order to examine whether or not GmPAP2.1 gene is related with the resistance against SMV, primary leaves of *Glycine max* were inoculated with pG5H:GFP, pG7H:GFP, pG5H:GFP-GmPAP2.1, or pG7H:GFP-GmPAP2.1, and 7 days, 14 days, and 21 days after the inoculation, accumulation level of the virus was examined based on the expression of GFP and viral RNA.

Figure 4A:
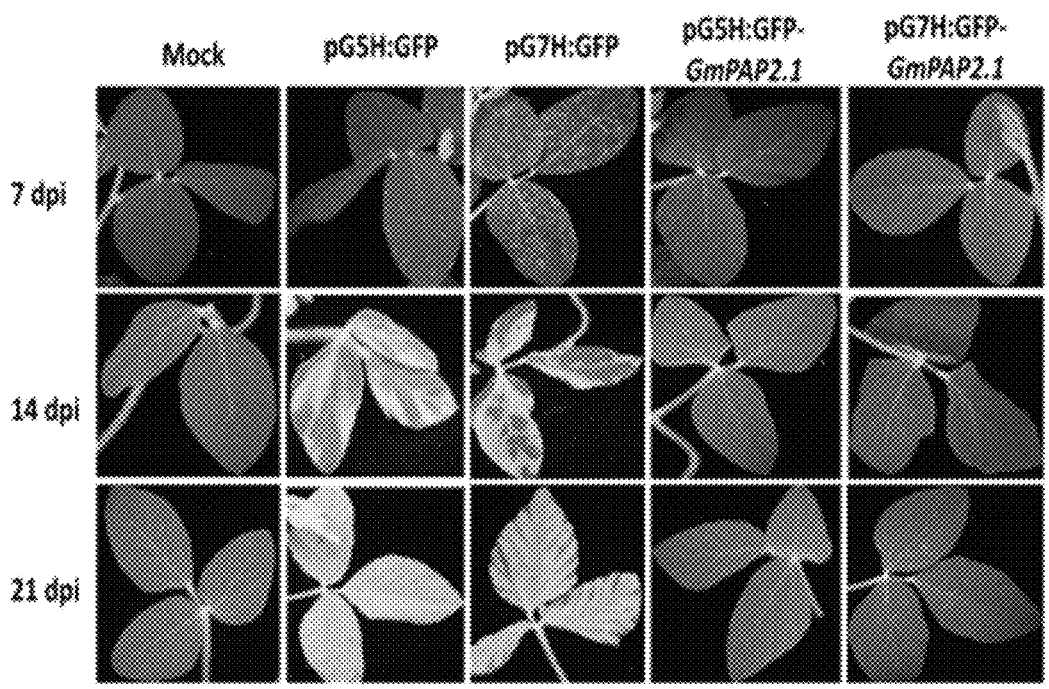
FIG. 4A shows the result of ultraviolet (UV) determination of expression level of GFP, which has been determined after inoculating pG5H:GFP, pG7H:GFP, pG5H:GFP-GmPAP2.1, or pG7H:GFP-GmPAP2.1 onto primary leaves of *Glycine max* to examine the disease resistance effect of GmPAP2.1 gene against SMV.

As a result, compared to Mock group treated with buffer only, a significantly increased expression of GFP and viral RNA is shown from the primary leaves inoculated with pG5H:GFP or pG7H:GFP while expression of GFP and viral RNA was hardly obtained from the primary leaves inoculated with pG5H:GFP-GmPAP2.1 or pG7H:GFP-GmPAP2.1, similar to Mock group (FIGS. 4A and 4B). Based on these results, it was realized that the disease resistance against SMV is enhanced as the expression of GmPAP2.1 gene increases.

Example 3. Analysis of GmPAP2.1 Domain Related to Disease Resistance Against SMV To analyze the disease resistance against SMV for each GmPAP2.1 domain, primary leaves of *Glycine max* were inoculated with pG5H:GFP, pG5H:GFP-GmPAP2.1 (full-length), pG5H:GFP-GmPAP2.1_N (C-terminal deletion: Δ257-409aa), or pG5H:GFP-GmPAP2.1_C (N-terminal deletion: Δ1-256aa), and 14 days after the inoculation, accumulation level of the virus was examined based on the expression of GFP and viral RNA.

Figure 5A:
FIG. 5A shows the result of UV determination of expression level of GFP, which has been determined after inoculating pG5H:GFP, pG5H:GFP-GmPAP2.1 (full-length), pG5H:GFP-GmPAP2.1_N (C-terminal deletion: Δ257-409aa) or pG5H:GFP-GmPAP2.1_C (N-terminal deletion: Δ1-256aa) onto primary leaves of *Glycine max* to examine the disease resistance effect against SMV for each domain of GmPAP2.1.
Figure 5B:
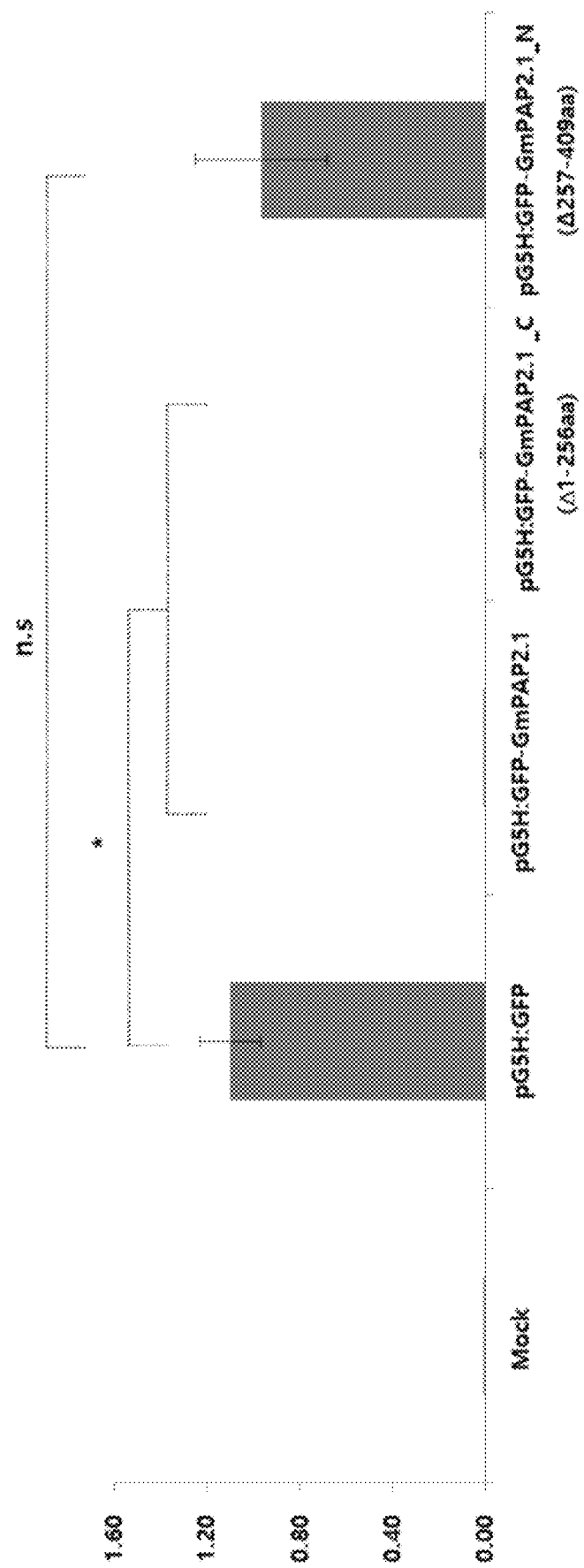
FIG. 5B shows a graph illustrating the expression level of viral RNA. For the statistical comparison between GFP-GmPAP2.1 or pG7H:GFP-GmPAP2.1 and positive control group pG5H:GFP or pG7H:GFP, unpaired 2-tailed T-test was employed (*:P<0.05, ns: P>0.05).

As a result, compared to Mock group, a significantly increased expression of GFP and viral RNA is shown from the primary leaves inoculated with pG5H:GFP while expression of GFP and viral RNA was hardly obtained from the primary leaves inoculated with pG5H:GFP-GmPAP2.1, similar to Mock group. However, from the primary leaves inoculated with pG5H:GFP-GmPAP2.1_N in which the C-terminal is deleted, a significantly increased expression of GFP and viral RNA is shown compared to the primary leaves of Mock group and also the primary leaves inoculated with pG5H:GFP-GmPAP2.1_C in which the N-terminal is deleted (FIGS. 5A and 5B). Based on these results, it was realized that the disease resistance against SMV is enhanced as the expression of GmPAP2.1 increases, and, in particular, the C-terminal of GmPAP2.1 is highly related to the resistance against SMV.

A sequence listing electronically submitted with the present application on Mar. 31, 2021 as an ASCII text file named 20210331_Q50321GR03_TU_SEQ, created on Mar. 24, 2021 and having a size of 9,000 bytes, is incorporated herein by reference in its entirety.

What is claimed is:

1. A method of enhancing disease resistance of a plant against Soybean mosaic virus compared to a non-transformant, the method comprising:
   transforming a plant cell of the plant with a recombinant vector containing a gene encoding Glycine max purple acid phosphatase 2.1 (GmPAP2.1) protein from Glycine max to overexpress the gene encoding the GmPAP2.1 protein,
   wherein the GmPAP2.1 protein consists of the amino acid sequence of SEQ ID NO: 2 or SEQ ID NO: 3, and
   the plant belongs to the family Fabaceae.

2. The method of claim 1, wherein the GmPAP2.1 protein consists of the amino acid sequence of SEQ ID NO: 2.

3. The method of claim 1, wherein the GmPAP2.1 protein consists of the amino acid sequence of SEQ ID NO: 3.

4. A method of producing a transgenic plant having enhanced disease resistance against Soybean mosaic virus compared to a non-transformant, the method comprising:
   transforming a plant cell with a recombinant vector containing a gene encoding Glycine max purple acid phosphatase 2.1 (GmPAP2.1) protein from Glycine max; and
   regenerating a plant from the transformed plant cell to produce the transgenic plant,
   wherein the GmPAP2.1 protein consists of the amino acid sequence of SEQ ID NO: 2 or SEQ ID NO: 3, and
   the plant belongs to the family Fabaceae.

5. The transgenic plant produced by the method of claim 4.

6. A transgenic seed of the transgenic plant of claim 5, wherein the transgenic seed comprises a transgene encoding GmPAP2.1 protein consisting of the amino acid sequence of SEQ ID NO: 2 or SEQ ID NO: 3.

* * * * *